Figures 3, 4:
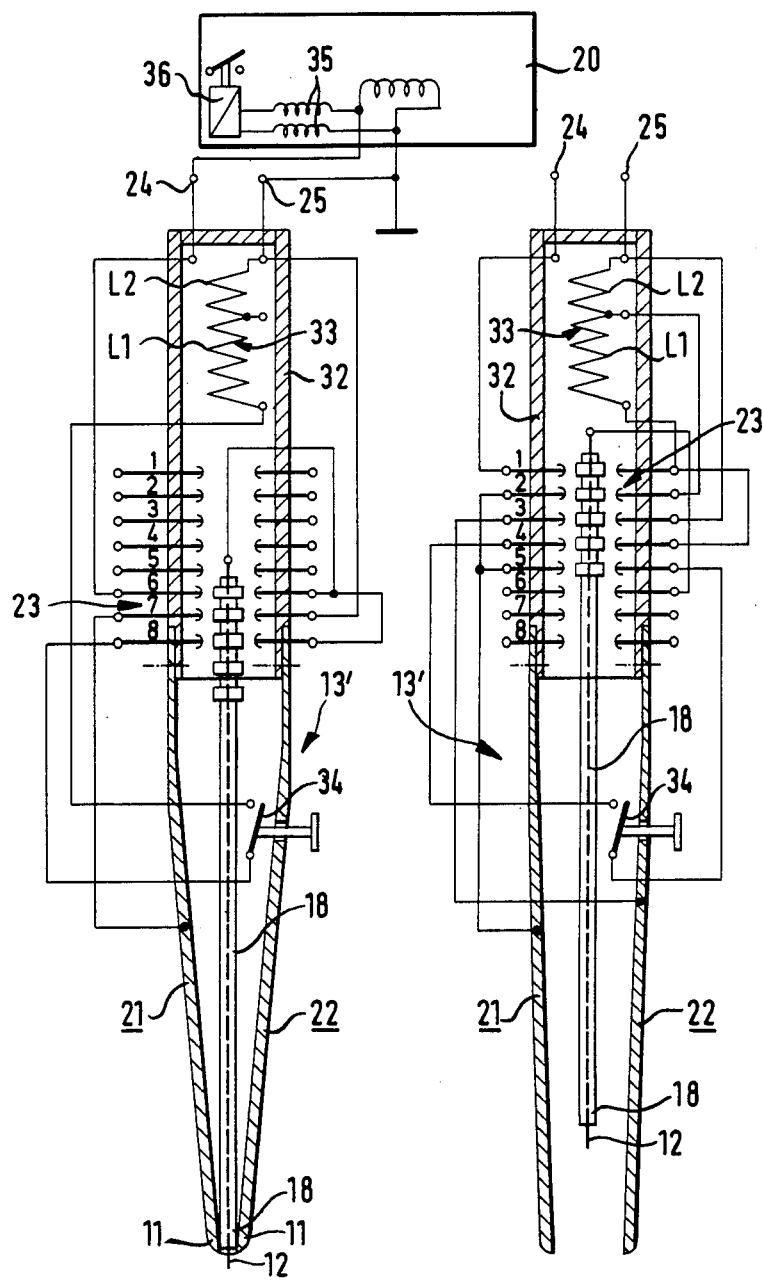

United States Patent [19]

Roos

[11] Patent Number: 4,706,667
[45] Date of Patent: Nov. 17, 1987

[54] ELECTRO SURGICAL HIGH FREQUENCY CUTTING INSTRUMENT

[75] Inventor: Eberhard Roos, Tuttlingen, Fed. Rep. of Germany

[73] Assignee: Berchtold Medizin-Elektronik GmbH & Co., Tuttlingen, Fed. Rep. of Germany

[21] Appl. No.: 892,883

[22] Filed: Jul. 28, 1986

Related U.S. Application Data

[62] Division of Ser. No. 747,086, Jun. 20, 1985.

[30] Foreign Application Priority Data

Jun. 25, 1984 [DE] Fed. Rep. of Germany ....... 3423356

[51] Int. Cl.⁴ .............................................. A61B 17/36
[52] U.S. Cl. ............................ 128/303.14; 128/303.17
[58] Field of Search ............ 128/303.1, 303.13–303.17

[56] References Cited

U.S. PATENT DOCUMENTS

| | | | |
|---|---|---|---|
| 2,708,933 | 5/1955 | August | 128/303.14 |
| 3,494,364 | 2/1970 | Peters | 128/303.17 |
| 3,685,518 | 8/1972 | Beverle et al. | 128/303.17 |
| 3,920,021 | 11/1975 | Hiltebrandt | 128/303.17 |
| 4,011,872 | 3/1977 | Komiya | 128/303.14 |
| 4,034,762 | 7/1977 | Gosen et al. | 128/303.17 |
| 4,043,342 | 8/1977 | Morrison | 128/303.14 |
| 4,202,337 | 5/1980 | Hren et al. | 128/303.14 |
| 4,228,800 | 10/1980 | Degler et al. | 128/303.14 |
| 4,274,413 | 6/1981 | Hahn et al. | 128/303.17 |
| 4,338,940 | 7/1982 | Ikuno | 128/303.17 |
| 4,476,862 | 10/1984 | Pao | 128/303.17 |

FOREIGN PATENT DOCUMENTS

2521719 11/1976 Fed. Rep. of Germany ... 128/303.1
2926630 1/1981 Fed. Rep. of Germany ... 128/303.1

Primary Examiner—William E. Kamm
Assistant Examiner—Max F. Hindenburg
Attorney, Agent, or Firm—Townsend and Townsend

[57] ABSTRACT

In an electro-surgical r.f. cutting instrument in which the neutral electrode (11) is arranged on both sides of the cutting electrode (12) but is however set back relative to the cutting electrode (12) on the instrument body (13). The ratio of the sizes of the contact areas (14, 15) of the neutral electrode (11) and of the cutting electrode (12) is greater than 7:1 and smaller than 20:1.

3 Claims, 4 Drawing Figures

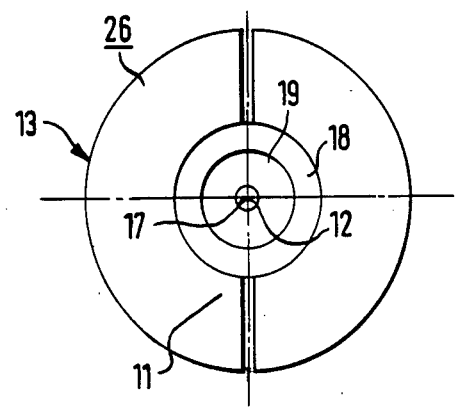
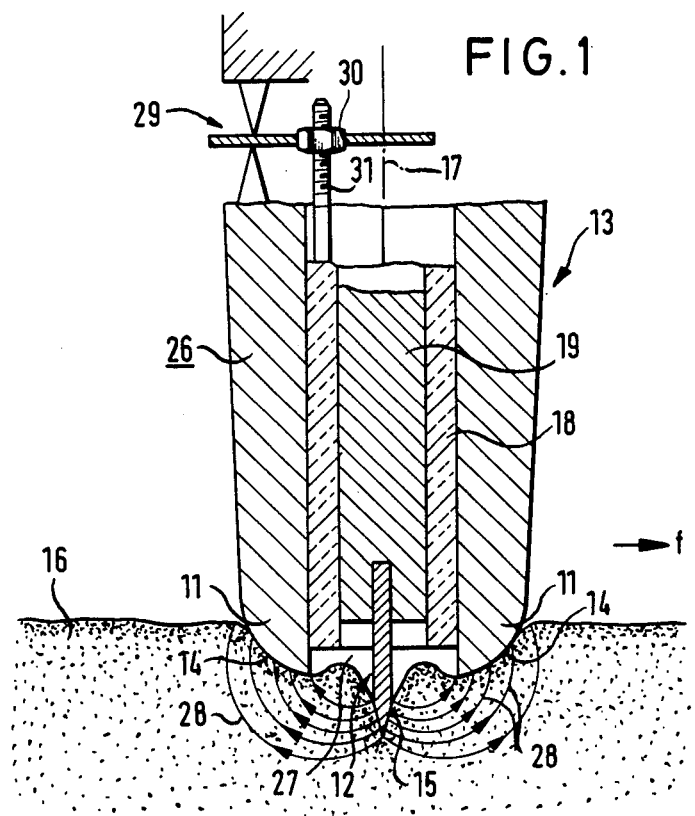

ELECTRO SURGICAL HIGH FREQUENCY CUTTING INSTRUMENT

This is a division of application Ser. No. 747,086, filed June 20, 1985.

The invention relates to an electro-surgical high frequency cutting instrument comprising a preferably elongate instrument body from which, in the operative state, a small area cutting electrode projects forwardly, and a large area neutral electrode which can be brought into contact with the patient near to the cutting electrode.

In a known electro-surgical high frequency cutting instrument of this kind (DE-OS No. 25 21 719) the neutral electrode is admittedly arranged in the immediate vicinity of the cutting electrode, it is however so separated from the tissue by a plastic cover, or by its arrangement in an endoscope, that it can only enter into electrical contact with the cutting electrode electrolytically via the secretion which is present during the cutting process. As a result, it is difficult to maintain the current intensity required for troublefree cutting in a required precisely defined manner at the cutting electrode. Thus, if the power setting at the r.f. generator is too high, burns can result or, if the power setting is too low, then a poor cut or indeed injury occurs because the tissue to be cut sticks to the cutting electrode as a result of coagulation processes.

The principal object of the invention is to provide an electro-surgical high frequency cutting instrument of the initially named kind in which current conditions which are largely precisely defined are present at the cutting electrode during the making of a cut substantially perpendicular to the longitudinal axis of the body of the instrument, with the current conditions ensuring a troublefree clean cut of the tissue without overheating of the tissue and without the tissue and the instrument sticking together.

In order to satisfy this object the invention provides that the neutral electrode is arranged on the instrument body on both sides of the cutting electrode, but set back relative to the cutting electrode, in such a way that it is supported on the tissue on both sides of the cutting electrode while the axially projecting cutting electrode penetrates into the tissue; and that the ratio of the sizes of the contact surfaces between the neutral electrode and the tissue on the one hand and between the cutting electrode and the tissue on the other hand, is greater than 7:1.

If, in a cutting instrument of this kind, a power of for example 5 to 10 Watts per $mm^2$ is applied to the cutting electrode then a power density occurs at the cutting electrode, which is preferably formed as a point, which is such that the heat necessary for tissue separation is generated in the tissue and in the tissue cells. The fact that the neutral electrode itself is likewise in current conducting contact with the tissue ensures a problem-free flow of current between the cutting electrode and the neutral electrode. In other words the transition resistance between the two electrodes is substantially constant. As a result of the larger area of the neutral electrode which is in contact with the tissue the power density at the neutral electrode is reduced so far that with normal cutting speeds of the order of several cm per sec. not even tissue heating, which could lead to coagulation, occurs. The neutral electrode thus slides smoothly over the tissue during cutting while the cutting electrode, which is arranged directly alongside or between it, causes the required strong heating at the desired location of the cut that is necessary to execute a smooth cut. As the resistance between the cutting electrode and neutral electrode is largely constant the high frequency power of the generator can be regulated to a value at which overheating of the tissue is also effectively avoided in the area of the cutting electrode, but such that a clean cut is nevertheless obtained.

The radiofrequency cutting instrument of the invention is uncritical in its operation by the surgeon because a problem-free electric cut is effected through the cutting electrode even with irregular cutting speed, without tissue damage or adhesion occurring in the region of the neutral electrode.

In order to prevent the cutting instrument of the invention from becoming awkward to handle provision should further be made that the ratio of the sizes of the contact areas of the neutral electrode and of the cutting electrode is smaller than 20:1 and preferably smaller than 15:1.

One obtains particularly good electro-surgical cutting characteristics combined with a compact and slim construction of the instrument body if the ratio of the sizes of the contact surfaces of the neutral electrode and of the cutting electrode is approximately 10:1.

Although the cutting electrode could also have the form of a narrow blade, it is preferred for the cutting electrode to project substantially axially and preferably also in a straight line from the tip of the instrument body. If the cutting electrode is in addition formed with a sharp tip then the power density in the tip region is particularly large which is important for a smooth cut free of injury.

The depth of cut preferably amounts to 0.5 to 5 mm. The extent of the neutral electrode which surrounds the cutting electrode in the direction perpendicular to the axis of the instrument body preferably amounts from 2 to 6, in particular from 3 to 5 and most particularly to approximately 4 mm.

The cutting speed conveniently amounts to from 1 to 5, in particular from 2 to 4 and preferably to approximately 3 cm/sec.

The distance of the cutting electrode from the neutral electrode in the direction perpendicular to the axis of the instrument body usefully amounts to from 5 to 15 and in particular to approximately 10 mm.

When the cutting electrode has a needle-like tip this tip preferably has a diameter from 0.1 to 0.5, in particular of from 0.2 to 0.4 and particularly of approximately 0.3 mm. The cutting electrode preferably projects axially beyond the neutral electrode by from 1 to 5 mm.

The tip of the cutting electrode can usefully have a length from 2 to 5 mm and preferably of approximately 3 mm.

As electrical insulation is necessary between the two electrodes a preferred practical embodiment is usefully arranged in such a way that the cutting electrode projects axially from an insulating body arranged inside the neutral electrode.

In order to increase the path for leakage currents between the two electrodes an advantageous further embodiment of the invention is characterised in that the insulating body is set back axially relative to the contact surface of the neutral electrode.

Furthermore, a practical realisation of the invention provides that the insulating body is formed as an insulating sleeve in which a metal rod is located which is connected to the generator and which carries the cutting electrode.

With this arrangement it is also expedient if the metal rod is set back axially relative to the neutral electrode, and preferably also relative to the insulating sleeve, in order to further reduce losses by leakage currents directly between the two electrodes.

It is of particular advantage if the cutting electrode is axially displaceably arranged on the instrument body. In this way the depth of cut can be preselected by the operator before performing an electric cut, with the range of adjustment being advantageously selectable between 0.5 and 5 mm.

In one realisation of the invention the neutral electrode can be circular cross-section and can concentrically surround the cutting electrode. In this case the instrument thus has approximately the shape of a pencil or stylus which can also be correspondingly held and guided by the operator. The metal tip which forms the cutting electrode projects from the bottom of the stylus at the center.

A further embodiment is constructed so that the neutral electrode is realised by the tips of the two limbs of a pincette or pair of tweezers which forms the insulating body. With this arrangement it is particularly expedient if the insulating sleeve with the cutting electrode can be retracted relative to the limbs of the pincette. In this manner the pincette can also be used without the cutting electrode of the invention.

Finally, this embodiment can be so further developed that the two branches of the pincette are insulated from one another, with a switch being provided which, when the cutting electrode and the insulating sleeve are retracted connects the limbs to the two voltage bearing terminals of the r.f. generator.

As a result of this construction the cutting instrument can also be used for coagulation, it being necessary to take appropriate electrical matching measures at the r.f. generator.

In order to ensure injury-free sliding of the neutral electrode on the tissue surface during the cut the contact surface of the neutral electrode should be of appropriate smooth and rounded shape. In particular, the neutral electrode is made of substantially hemispherical rounded shape at its end which enters into contact with the tissue.

The invention will now be described in the following by way of example only and with reference to the drawing which shows:

FIG. 1 a partially sectioned sideview of an electrosurgical radio frequency cutting instrument in accordance with the invention in the tip region which contacts the tissue 16 of a patient, FIG. 2 a view of the r.f. cutting instrument of FIG. 1 from below, FIG. 3 a schematic, partially sectioned sideview of a further embodiment of and r.f. cutting instrument in accordance with the invention and shaped like a pincette, and FIG. 4 a view similar to FIG. 3 of the same cutting instrument after switching over into the position provided for effecting coagulation.

As seen in FIGS. 1 and 2 a thin metal tip is used at the bottom of a cylindrical metal rod 19 as the cutting electrode 12. The cutting electrode 12 projects downwardly significantly beyond the metal rod 19. The metal rod 19 is concentrically sleeved by an insulating sleeve 18 which consists of a highly heat-resistant refractory ceramic or teflon material. A thick-walled metal tube 26 is arranged in narrow contact around the insulating sleeve 18 and can be put together of two half shells as shown in FIG. 2. The metal tube is formed at the lower or front end of the instrument body 13 formed in this way as a semi-spherical head which forms the neutral electrode 11. The design of the neutral electrode 11 with a semi-spherical head has the purpose of ensuring better sliding on the tissue 16 during cutting in the direction of the arrow f in FIG. 1.

The metal rod 19, the insulating sleeve 18 and the neutral electrode 11 are axially displaced relative to one another in stepped manner in accordance with FIG. 1 in such a way that the path for leakage current between the metal rod 19 and the neutral electrode 11 is as long or large as possible. Moreover, a distinct intermediate space 27 should be formed between the tissue surface and the front end face of the metal rod 19 when placing the instrument body 13 onto the tissue 16 in accordance with FIG. 1, so that current largely flows starting from the tip of the cutting electrode 12 into the tissue 16.

The metal tube 26, the insulating sleeve 18 and the metal rod 19 with the cutting electrode 12 together form an arrangement concentric to the axis 17.

The metal rod 19 is connected to the one terminal of an r.f. generator (not shown) and the metal tube 26 to the other pole of the r.f. generator, which has a floating output not coupled to earth.

The manner of operation of the r.f. cutting instrument in accordance with the invention is as follows: The instrument is first of all placed in accordance with FIG. 1 onto the tissue 16 which is to be separated by means of a cut, with a concave ring-like contact surface 14 being formed between the tissue 16 and the neutral electrode 11 and with a very small funnel-like contact surface 15 being formed between the tip of the cutting electrode 12 and the tissue 16. If the r.f. generator is now switched on then an r.f. current indicated by the current lines 28 flows between the cutting electrode 12 and the neutral electrode 11.

The dimensioning of the cutting electrode 12 and of the neutral electrode 11 is so selected that the contact areas 14, 15 have a ratio of approximately 10:1. If the instrument body 13 is now moved in the direction of the arrow f at a speed of approximately 3 cm/sec. over the tissue then a clean cut corresponding to the depth of penetration of the cutting electrode 12 will be formed in the tissue 16 without overheating or even adhesion occurring at the contact surface, because the current density close to the cutting electrode 12 is very high but rapidly reduces at a distance therefrom.

In order to adjust the depth of cut it is possible, in accordance with the invention, to axially displace either the metal rod 19 within the insulating sleeve 18 or, as assumed in FIG. 1, the insulating sleeve 18 within the metal tube 26, and to select a predetermined axial position relative to the metal tube 26 by an adjustment mechanism 29. The adjustment mechanism can for example consist of an adjustment nut 30 provided with a circular actuation disk which is arranged concentrically thereto, and of a threaded rod 31 which is connected with the insulating sleeve 18 for the transmission of axial forces. If the nut 30 is axially fixed to the metal tube 26, as indicated in FIG. 1, then really insulating sleeve 18 will be axially displaced relative to the metal tube 26 on rotation of the nut 30, which leads to a greater or lesser degree of projection of the cutting electrode 12 beyond the neutral electrode 11. The operator can thus predetermine the cutting depth with which he wants to operate. This possibility of adjustment is particularly important because for certain electric operations the danger exists that on cutting too deeply into the tissue layers other organs will be unintentionally injured. By selecting particularly shallow depths of cut using the adjustment mechanism of the invention such injuries can be completely avoided without particular attention being required by the surgeon during electric cutting.

As seen in FIGS. 3 and 4 the neutral electrode 11 which surrounds the cutting electrode 12 on both sides is formed by the tip regions of the two limbs 21, 22 of a pincette 13', with the two limbs being mounted in the upper region on an insulating cap 32.

The insulating sleeve containing the metal rod 19 and the cutting electrode 12 is axially displaceably arranged within the insulating cap 32 in a manner not shown in such a way that it is either approximately flush with the neutral electrode 11 in the position of FIG. 3, with the cutting electrode 12 projecting axially forwardly in similar manner to that shown in FIG. 1, or lies clearly behind the ends of the limbs as shown in FIG. 4, so that the pincette 32 can also be used as a normal clamping instrument.

When the insulating sleeve 18 is advanced in accordance with FIG. 3 a r.f. cutting instrument in accordance with the invention is created in which the two limbs 21, 22 can be pressed from both sides against the insulating sleeve 18 by finger pressure.

A coil 33 with two windings L1 and L2 is built into the insulating cap 32. The one terminal of the winding L2 is connected with the earthed terminal 25 of the r.f. generator 20. The other terminal of the winding L2, which simultaneously produces the connection to the winding L1 is connected, in accordance with FIG. 4, to one contact of a closing switch 2 which forms one element of a multiple switch 23 actuated by displacement of the insulating sleeve 18. The other terminal of the winding L1 is connected with the one contact of the first normally open switch 1 (FIG. 4) and with the one contact of a further switch 4 of the multiple switch 23.

It should be pointed out that, for the sake of clarity, only those line connections are shown in FIGS. 3 and 4 which are necessary for the operation of the relevant switch position. In actual fact the electrical line connections which can be seen by jointly viewing FIGS. 3 and 4 are present between the various components.

The multiple switch 23 has in total eight fixed contact pairs and five displacement contacts which are located between the contact pairs on the insulating sleeve 18, which form the individual switches 1 to 8.

The other (left hand) contact of the individual switch 1 is connected with the hot terminal 24 of the r.f. generator 20. The other contact of the switch 2 is electrically conductively connected with the other contact of the switch 5 and also with the limb 21. The switch 3 is connected on the one side with the earthed terminal 25 of the r.f. generator 20 and on the other side with the limb 22 of the pincetta 13'. The contacts of the switch 4 are connected to the one contact of the switch 1 and to the one contact of the hand switch 34. The contacts of the switch 5 are connected to the other contact of the hand switch 34 and to the other contact of the switch 2 and to the limb 21 respectively. The contacts of the switch 6 are connected to the cutting electrode 12 and to the one contact of the switch 8 and to the hot terminal 24 of the r.f. generator 20 respectively. The contacts of the switch 7 are connected to the earthed terminal 25 of the r.f. generator 20 and to the limb 21 respectively. The contacts of the switch 8 are connected with the one contact of the switch 5 and with the mentioned second contact of the hand switch 34 respectively.

The hand switch 34 serves to switch on the r.f. generator 20.

In the cutting position of FIG. 3 the full high frequency voltage is applied between the cutting electrode 12 and the neutral electrode 11 formed by the tip regions of the limbs 21, 22. The current flow from the r.f. generator 20 takes place via the poles 24, 25 in the manner shown in FIG. 3.

In accordance with the invention a low frequency control current with a low voltage is superimposed on the r.f. current. If the hand switch 34 is closed then this low frequency control current flows via the windings of the coil 33 which acts as an r.f. filter and further r.f. coupling coils 35 to a schematically illustrated switching relay 36 in the r.f. generator 20 which switches on the r.f. generator 20 when it engages. Thus, the r.f. generator 20 can be set in operation by closing the hand switch 34.

While the sliding contacts on the insulating sleeve 18 only close the switches 6, 7 and 8 in the cutting position of FIG. 3 these three switches are open in the coagulating position of FIG. 4 and in their place the switches 1 to 5 are closed. The insulating sleeve 18 is retracted in this position sufficiently far that the cutting electrode 11, which is here shaped like a needle, cannot come into contact with the tissue.

In the switch position of FIG. 4 the full r.f. voltage of the r.f. generator 20 is applied to the windings of the coil 33. The two limbs 21, 22 of the pincette are fully electrically insulated from one another in this position and receive a reduced r.f. voltage from the winding L2 of the coil 33. The voltage is thus stepped down (transformed).

If tissue is now clamped between the tip regions of the limbs 21, 22 and the r.f. generator 20 is again connected by closing the hand switch 34 then a r.f. current flows through the branches 21, 22 into the tissue and there generates the electrical heat losses necessary for coagulation.

In the switch position of FIG. 4 a low frequency control current for the switch-in relay 36 which is superimposed on the r.f. current also flows via the winding L1 of the coil 33 with L1 forming an element of a resonant circuit.

The load impedance for the cutting of FIG. 3 and for the coagulation of FIG. 4 is different. Whereas one can reckon with a load impedance of ca. 1000 Ohms during cutting the load impedance during coagulation amounts to approximately 50 to 100 Ohms. In order to obtain troublefree functioning in the various switch positions the output oscillating circuit of the r.f. generator 20 must be matched to these conditions respectively.

A particular advantage of the embodiment of FIGS. 3 and 4 lies in the fact that in the position of use for the cutting process the characteristic of the r.f. generator required for this application can be brought into effect, namely that the power increases with increasing resistance. In the position of use for coagulation in accordance with FIG. 4 a power characteristic results, brought about by the winding L2 of the coil 33, such that the power drops off with increasing resistance.

The r.f. generator 20 can also have an output decoupled from earth (floating output) with terminal 25 then no longer being connected to earth as shown in FIG. 3.

One of the essential advantages of the bipolar application technique of the invention is the reduced flow of leakage currents to earthed parts of the operating table which has been reduced to a non-dangerous minimum by the freedom of the patient current circuit from earthing and ground leaks.

I claim:

1. An electro-surgical apparatus for connecting to first and second outputs of an electrical generator comprising:
   a first electrode comprising first and second generally elongate members, the members being spaced apart at one end and being displaceable relative to each other at the other end;
   a second electrode disposed between the first and second members of the first electrode and beign generally parallel thereto;
   means for displacing the second electrode relative to the first electrode;
   means for connecting the first output of the electrical generator to the first and second members of the first electrode and for connecting the second output of the electrical generator to the second electrode when the second electrode is displaced to a first position relative to the first electrode; and
   means for alternately connecting the first output of the electrical generator to the first member of the first electrode and for connecting the second output of the electrical generator to the second member of the first electrode when the second electrode is displaced to a second position relative to the first electrode.

2. The apparatus according to claim 1 further comprising:
   means for electrically insulating the members of the first electrode from each other; and
   means for connecting the first output of the electrical generator to the first member of the first electrode and for connecting the second output of the electrical generator to the second member of the first electrode.

3. The apparatus according to claim 1 further comprising:
   means for applying a first voltage to the first and second electrodes when the second electrode is displaced to the first position relative to the first electrode; and
   means for applying a second voltage to the first and second members of the first electrode when the second electrode is displaced to the second position relative to the first electrode.

* * * * *